United States Patent

Mikami et al.

[11] Patent Number: 5,914,418
[45] Date of Patent: Jun. 22, 1999

[54] POLYMERIZATION INHIBITOR FOR ACRYLIC-FUNCTIONAL SILANES

[75] Inventors: Ryuzo Mikami; Tadashi Okawa, both of Chiba Prefecture, Japan

[73] Assignee: Dow Corning Toray Silicone Co., Ltd., Tokyo, Japan

[21] Appl. No.: 08/839,587

[22] Filed: Apr. 15, 1997

[30] Foreign Application Priority Data

Apr. 26, 1996 [JP] Japan .................................. 8-131431

[51] Int. Cl.$^6$ .............................. C07F 7/12; C09K 15/20; C09K 15/32
[52] U.S. Cl. ................ 556/401; 252/182.29; 252/400.2; 252/400.54; 252/400.62; 252/403; 252/404; 252/406
[58] Field of Search ................. 252/403, 400.2, 252/400.54, 400.62, 404, 406, 182.29; 556/401, 70, 87; 570/119; 564/336, 343; 568/716

[56] References Cited

U.S. PATENT DOCUMENTS

| | | | |
|---|---|---|---|
| 3,305,483 | 2/1967 | Coffield | 252/42.4 |
| 4,477,326 | 10/1984 | Lin | 204/159.13 |
| 5,103,032 | 4/1992 | Turner et al. | 556/401 |
| 5,262,555 | 11/1993 | Okawa et al. | 556/440 |
| 5,286,772 | 2/1994 | Rapoport | 524/345 |
| 5,493,039 | 2/1996 | Okawa et al. | 556/440 |

FOREIGN PATENT DOCUMENTS 5-301881 11/1993 Japan .
7-025907 1/1995 Japan .

Primary Examiner—Richard D. Lovering
Attorney, Agent, or Firm—William F. Boley

[57] ABSTRACT

A method for inhibiting polymerization of acrylic-functional silanes comprising forming a mixture comprising an acrylic-functional silane and a polymerization inhibitor described by formula

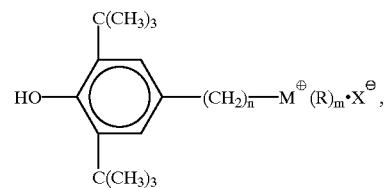

where n is 0 or 1; M is an atom selected from a group consisting of N, P, As, Sb, O, S, Se, Sn, and I; R is an independently selected monovalent hydrocarbon group or hydrogen atom; m is 1, 2, or 3; and X is a conjugate base of an organic acid or inorganic acid.

10 Claims, No Drawings

POLYMERIZATION INHIBITOR FOR ACRYLIC-FUNCTIONAL SILANES

BACKGROUND OF INVENTION

This invention relates to a method for inhibiting polymerization of acrylic-functional silanes. More particularly, this invention relates to a polymerization inhibitor that can inhibit the polymerization of acrylic-functional silanes.

Acrylic-functional silanes, e.g., acryloxy group-containing silanes, methacryloxy group-containing silanes, and the like, readily react with radical-polymerizable monomers, such as methyl methacrylate and styrene, and as a consequence are used as starting materials for copolymers derived from these monomers and as modifiers for polymers obtained from these monomers.

Acrylic-functional silanes can be prepared by an addition reaction between a SiH-functional halosilane and the acrylate or methacrylate ester of an alcohol or phenol that contains an aliphatically unsaturated bond. The desired acrylic-functional silane is then isolated from the resulting mixture by distillative purification. Refer in this regard to, for example, Japanese Patent Application Kokai Number Hei 5-301881 (301,881/1993). However, this addition reaction and isolation by distillative purification has been encumbered by severe difficulties because compounds of this type readily polymerize upon heating and as a result can become highly polymerized during the reaction and distillation stages. This problem has made it quite difficult to obtain high-purity acrylic-functional silanes in high yields. Therefore it is necessary to run the addition reaction in these methods at a reaction temperature at which thermal polymerization will not occur. However, this type of temperature control is quite difficult and the reaction product often ends up becoming highly polymerized and gelled.

The addition of a hindered phenol, amine compound, or quinone compound to the reaction system has also been proposed as a method for inhibiting the polymerization and gelation of acrylic-functional silanes. For example, Japanese Patent Application Kokai number Hei 7-25907 (25,907/1995) describes a substantial improvement in thermal stability for the addition of 2,6-di-tert-butyl-4-hydroxymethylphenol to a crude mixture prepared from γ-methacryloxypropyltrichlorosilane and methanol whose main component is γ-methacryloxypropyltrimethoxysilane. This inhibitor, however, does not provide a complete inhibition of gelation during the addition reaction between a SiH-functional halosilane and the acrylate or methacrylate ester of an aliphatically unsaturated alcohol or phenol. In addition, Japanese Patent Application Kokai Number Hei 5-186478 (186,478/1993) has proposed the use of N,N-dialkylaminomethylenephenol as a polymerization inhibitor. This inhibitor performs relatively well in terms of inhibiting the polymerization of acrylic-functional silanes and halosilanes. However, it acts as a catalyst poison for the platinum catalysts used as the addition-reaction catalyst in the preparation of these silanes by the above-described addition reaction, with the result that large amounts of platinum catalyst must be employed in order to complete the reaction.

The inventors achieved the present invention as a result of extensive investigations directed to solving the problems described above. Specifically, the object of the present invention is to provide a novel polymerization inhibitor that can inhibit the polymerization of acrylic-functional silane during their synthesis, purification, and storage. The polymerization inhibitors according to the present invention has an inhibiting effect superior to that of known polymerization inhibitors.

SUMMARY OF INVENTION

A method for inhibiting polymerization of acrylic-functional silanes. The method of inhibiting polymerization of acrylic-functional silanes comprises forming a mixture comprising an acrylic-functional silane and a polymerization inhibitor described by formula

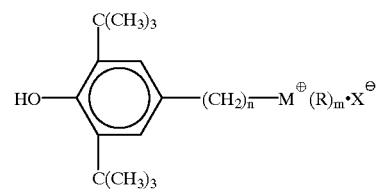

where n is 0 or 1; M is an atom selected from a group consisting of N, P, As, Sb, O, S, Se, Sn, and I; R is a monovalent hydrocarbon group or hydrogen atom; m is 1, 2, or 3; and X is a conjugate base of an organic acid or inorganic acid.

DESCRIPTION OF INVENTION

The present invention is a method for inhibiting polymerization of acrylic-functional silanes comprising forming a mixture comprising an acrylic-functional silane and a polymerization inhibitor described by formula (1)

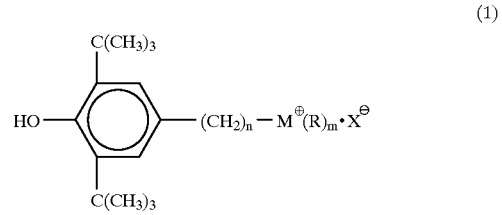

where n is 0 or 1; M is an atom selected from the group consisting of N, P, As, Sb, O, S, Se, Sn, and I; R is a monovalent hydrocarbon group or hydrogen atom; m is 1, 2, or 3; and X is a conjugate base of an organic acid or inorganic acid.

In formula (1), R can be a hydrogen atom or a monovalent hydrocarbon group, and examples of the latter are alkyl groups such as methyl, ethyl, and propyl; alkenyl groups such as vinyl, allyl, and butenyl; aryl groups such as phenyl, tolyl, and xylyl; and aralkyl groups such as phenylethyl and diphenylmethyl. Methyl and hydrogen are preferred for R.

In formula (1), M is an atom selected from the group consisting of N, P, As, Sb, O, S, Se, Sn, and I. In formula (1), while m in general has a value of 1, 2, or 3, m will be 3 when M is N, P, As, or Sb; 2 when M is O, S, Se, or Sn; and 1 when M is I. In formula (1), X refers to the conjugate base of an organic or inorganic acid and is exemplified by halogen ions, which are the conjugate bases of hydrogen halides such as hydrogen chloride and hydrogen bromide; by the conjugate bases of carboxylic acids such as acetic acid, propionic acid, and acrylic acid; and by the conjugate bases of sulfuric acid, sulfonic acid, and phosphoric acid.

The compounds described by formula (1) are exemplified by compounds with the following molecular structures, in which R and X are as defined above.

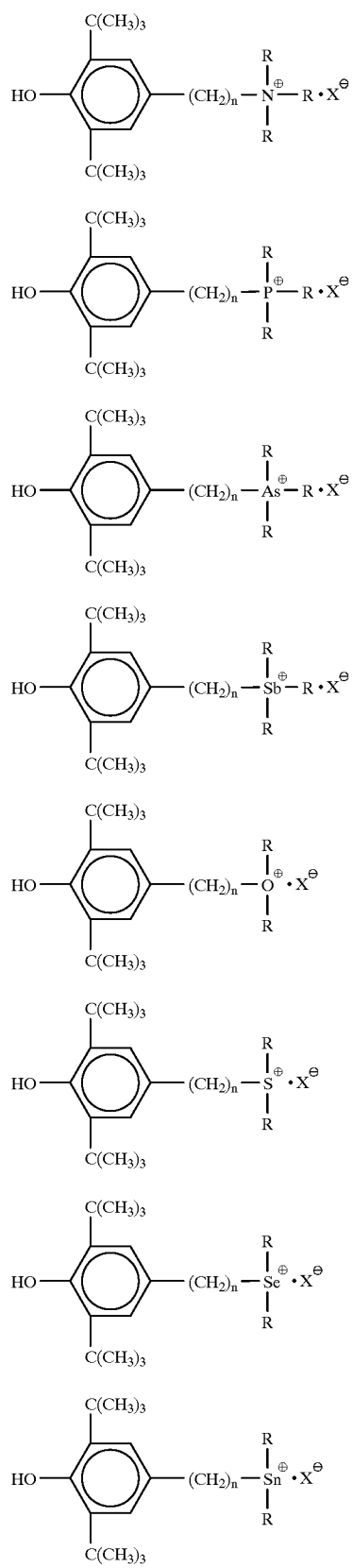

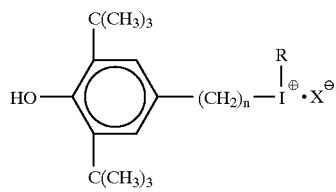

The polymerization inhibitors according to the present invention have chemical structures as defined above. Polymerization inhibitors with the following chemical structures are preferred. R in the following chemical structures is the hydrogen atom or a monovalent hydrocarbon group as described above.

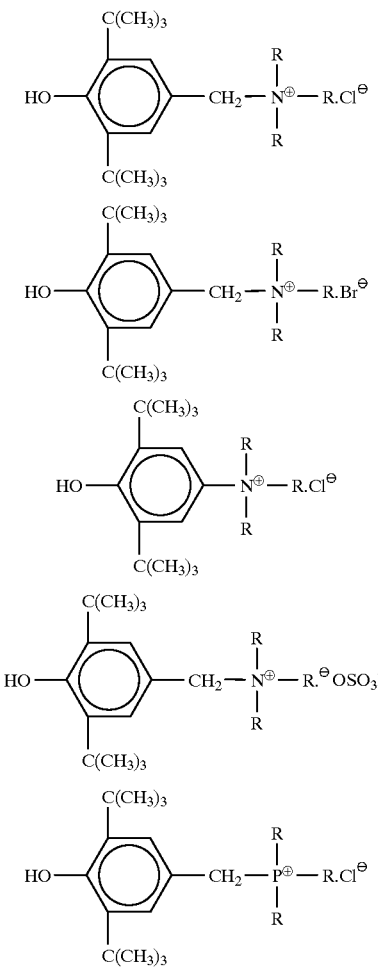

Polymerization inhibitors according to the present invention are easily synthesized by well-known methods in which an organic acid or inorganic acid or organic halide is reacted with the corresponding substituted or unsubstituted phenol-containing Lewis base.

Acrylic-functional silanes to which the polymerization inhibitor according to the present invention may be applied are exemplified by methacryloxy-functional silanes such as 3-methacryloxypropyldimethylchlorosilane, 3-methacryloxypropylmethyldichlorosilane, and 3-methacryloxypropyltrichlorosilane, and by acryloxy-functional silanes such as 3-acryloxypropyldimethylchlorosilane, 3-acryloxypropylmethyldichlorosilane, and 3-acryloxypropyltrichlorosilane.

The invention will be explained in greater detail below through working examples.

SYNTHESIS EXAMPLE 1

A clear mixture comprising 1 g (3.8 mmol) 2,6-di-tert-butyl-4-dimethylaminomethylphenol, 0.76 g (8.4 mmol) trimethylsilanol, and 30 mL toluene was formed. Then, 0.46 g (4.2 mmol) of trimethylchlorosilane was added dropwise to this mixture while stirring forming a white precipitate. After stirring for 30 minutes at room temperature, the white precipitate was filtered off, washed with toluene, and dried under vacuum at 80° C. for 1 hour to give 0.7 g of the white precipitate. Analysis of the white precipitate by nuclear magnetic resonance analysis (NMR) and infrared absorption analysis (IR) confirmed it to be 3,5-di-tert-butyl-4-hydroxyphenylmethyldimethylammonium chloride as described by formula

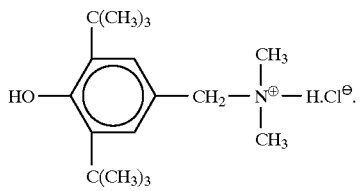

EXAMPLE 1

The following were introduced into and mixed in a 30-mL stopper-equipped glass bottle: 10 g 3-methacryloxypropyldimethylchlorosilane, 0.5 g dimethylchlorosilane, and 0.038 g (0.127 mmol) of the 3,5-di-tert-butyl-4-hydroxyphenylmethyldimethylammonium chloride as described in Synthesis Example 1. This was followed by the introduction of a platinum catalyst in the form of a complex of chloroplatinic acid and 1,3-divinyltetramethyldisiloxane. The platinum catalyst was added in sufficient quantity to provide 10 ppm platinum metal based on the 3-methacryloxypropyldimethylchlorosilane. The bottle was then sealed with a stopper after purging with nitrogen. The dimethylchlorosilane and platinum catalyst were added to promote polymerization of the 3-methacryloxypropyldimethylchlorosilane, as already described by the inventors in Japanese Patent Application Kokai Number Hei 6-107715 (107,715/1994). The glass bottle was held in a temperature controlled oil bath at 150° C. in order to measure the gelation time of the content. As used herein, the gelation time refers to the time required for the content to lose its fluidity and thereby gel. The results are reported in Table 1.

COMPARATIVE EXAMPLES 1 TO 6

The gelation time was measured as described for Example 1, but in each case using 0.127 mmol of the polymerization inhibitor specified in Table 1 in place of the 3,5-di-tert-butyl-4-hydroxyphenylmethyldimethylammonium chloride. These results are also reported in Table 1.

EXAMPLE 2

The following were introduced into and mixed in a 30-mL stopper-equipped glass bottle: 10 g 3-methacryloxypropyldimethylchlorosilane, 0.5 g dimethylchlorosilane, and 0.076 g (0.254 mmol) of the 3,5-di-tert-butyl-4-hydroxyphenylmethyldimethylammonium chloride is described in Synthesis Example 1. This was followed by the introduction of a platinum catalyst in the form of a complex of chloroplatinic acid and 1,3-divinyltetramethyldisiloxane. The platinum catalyst was added in sufficient quantity to provide 10 ppm platinum metal based on the 3-methacryloxypropyldimethylchlorosilane. The bottle was then sealed with a stopper after purging with nitrogen. The dimethylchlorosilane and platinum catalyst were added to promote polymerization of the 3-methacryloxypropyldimethylchlorosilane, as proposed by the inventors in Japanese Patent Application Laid Open Kokai Number Hei 6-107715. The glass bottle was held in a temperature controlled oil bath at 150° C. in order to measure the gelation time of the content. 30 hours were required for the content to lose its fluidity and become a gel.

TABLE 1

| | polymerization inhibitor | addition (mmol) | gelation time (hours) |
|---|---|---|---|
| Example 1 | 3,5-di-tert-butyl-4-hydroxyphenylmethyldimethyl-ammonium chloride | 0.127 | 20 |
| Comparative Example 1 | 3,5-di-tert-butyl-4-hydroxyanisole | 0.127 | 0.25 |
| Comparative Example 2 | 2,6-di-tert-butyl-4-methylphenol | 0.127 | 0.5 |
| Comparative Example 3 | 3,5-di-t-butyl-4-hydroxybenzaldehyde | 0.127 | 3 |
| Comparative Example 4 | 2,6-di-tert-butyl-4-hydroxymethylphenol | 0.127 | 3.5 |
| Comparative Example 5 | 2,6-di-tert-butyl-4-dimethylaminomethylphenol | 0.127 | 12.5 |
| Comparative Example 6 | benzyldimethylammonium chloride | 0.127 | <0.25 |

We claim:

1. A method of inhibiting polymerization of acrylic-functional silanes comprising forming a mixture comprising an acrylic-functional silane and a polymerization inhibitor described by formula

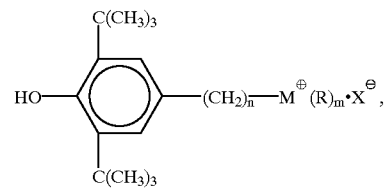

where n is 0 or 1; M is an atom selected from the group consisting of N, P, As, Sb, O, S, Se and Sn; R is a monovalent hydrocarbon group or hydrogen atom; m is 1, 2, or 3; and X is a conjugate base of an organic acid or inorganic acid.

2. A method according to claim 1, where the polymerization inhibitor is described by formula

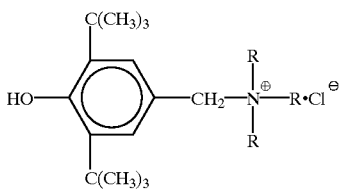

where R is a monovalent hydrocarbon group or hydrogen atom.

3. A method according to claim 1, where the polymerization inhibitor is described by formula

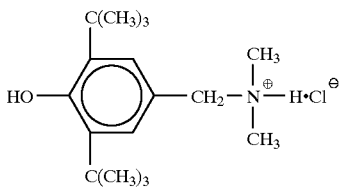

4. A method according to claim 1, where the acrylic-functional silane is 3-methacryloxypropyldimethylchlorosilane.

5. A method according to claim 1, where m is 3 and M is selected from the group consisting of N, P, As, and Sb.

6. A method according to claim 1, where m is 2 and M is selected from the group consisting of O, S, Se, and Sn.

7. A method according to claim 1, where m is 1 and M is I.

8. A method according to claim 1, where X is the conjugate base of a hydrogen halide.

9. A method according to claim 1, where X is the conjugate base of a carboxylic acid.

10. A method according to claim 1, where X is a conjugate base of an inorganic acid selected from the group consisting of sulfuric acid, sulfonic acid, and phosphoric acid.

* * * * *